United States Patent
Utsumi et al.

(10) Patent No.: US 10,105,112 B2
(45) Date of Patent: Oct. 23, 2018

(54) X-RAY GENERATING TUBE, X-RAY GENERATING APPARATUS, AND RADIOGRAPHY SYSTEM

(71) Applicant: CANON KABUSHIKI KAISHA, Tokyo (JP)

(72) Inventors: Kazushige Utsumi, Sagamihara (JP); Nobuhiro Ito, Yamato (JP); Kazuyuki Ueda, Tokyo (JP); Kazuya Tsujino, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 199 days.

(21) Appl. No.: 15/022,905

(22) PCT Filed: Sep. 10, 2014

(86) PCT No.: PCT/JP2014/004659
§ 371 (c)(1),
(2) Date: Mar. 17, 2016

(87) PCT Pub. No.: WO2015/040829
PCT Pub. Date: Mar. 26, 2015

(65) Prior Publication Data
US 2016/0228076 A1    Aug. 11, 2016

(30) Foreign Application Priority Data
Sep. 19, 2013    (JP) .................. 2013-193903

(51) Int. Cl.
*H01J 35/08*    (2006.01)
*A61B 6/00*    (2006.01)
(Continued)

(52) U.S. Cl.
CPC .............. *A61B 6/4028* (2013.01); *A61B 6/02* (2013.01); *A61B 6/025* (2013.01); *A61B 6/032* (2013.01);
(Continued)

(58) Field of Classification Search
CPC .. H01J 35/00; H01J 35/02; H01J 35/08; H01J 35/14; H01J 35/16; H01J 2235/00;
(Continued)

(56) References Cited

U.S. PATENT DOCUMENTS

| 7,551,722 B2* | 6/2009 | Ohshima ................ G01N 23/04 378/143 |
| 2012/0318987 A1* | 12/2012 | Miyazaki ................ H01J 35/08 250/358.1 |
| 2013/0230143 A1* | 9/2013 | Ueda ....................... H01J 35/18 378/62 |

FOREIGN PATENT DOCUMENTS

| JP | H07-260713 A | 10/1995 |
| JP | 2003-505845 A | 2/2003 |

(Continued)

*Primary Examiner* — Jurie Yun
(74) *Attorney, Agent, or Firm* — Canon USA, Inc. I.P. Division

(57) ABSTRACT

An X-ray generating tube including a transmission target having a minute focal spot. The X-ray generating tube includes a transmission target having a first surface configured to be irradiated with an electron beam; an electron emitting source configured to irradiate the transmission target with the electron beam obliquely; and a tubular forward shield member to define an extraction angle of an extracted X-ray beam. The forward shield member is disposed such that a central axis of the electron beam and a central axis of the X-ray beam whose extraction angle is defined are located at the same side with respect to a virtual normal plane perpendicular to the surface and a projection of the central axis of the electron beam to the surface.

19 Claims, 15 Drawing Sheets

(51) Int. Cl.
*A61B 6/02* (2006.01)
*A61B 6/03* (2006.01)
*G21K 1/02* (2006.01)

(52) U.S. Cl.
CPC ............ *A61B 6/4085* (2013.01); *A61B 6/502* (2013.01); *G21K 1/02* (2013.01); *H01J 35/08* (2013.01); *A61B 6/54* (2013.01); *H01J 2235/087* (2013.01); *H01J 2235/165* (2013.01)

(58) Field of Classification Search
CPC . H01J 2235/086; H01J 2235/087; A61B 6/00; A61B 6/02; A61B 6/03; A61B 6/025; A61B 6/4028; A61B 6/502; A61B 6/032; A61B 6/4085
USPC .......... 378/37, 119, 121, 122, 141, 142, 203
See application file for complete search history.

(56) References Cited

FOREIGN PATENT DOCUMENTS

| | | |
|---|---|---|
| JP | 2007-97610 A | 4/2007 |
| JP | 2009-545840 A | 12/2009 |
| JP | 2012-124098 A | 6/2012 |
| JP | 2012-138168 A | 7/2012 |
| WO | 2005/098871 A1 | 10/2005 |

\* cited by examiner

[Fig. 1]
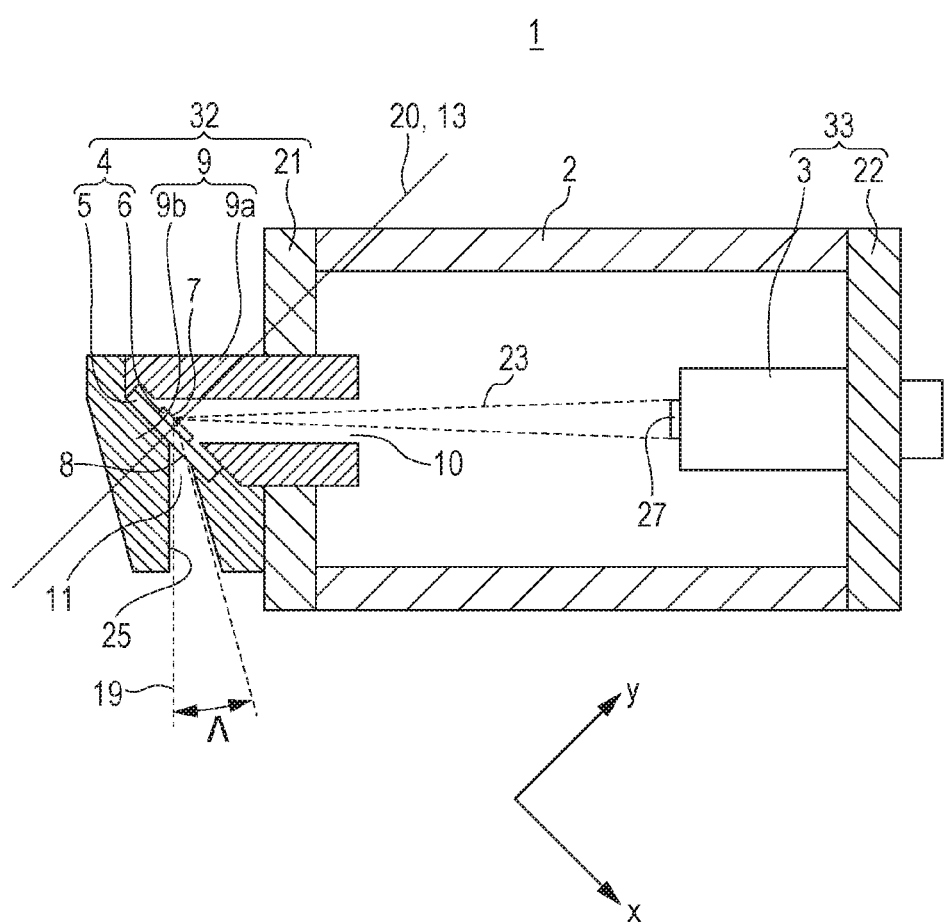

[Fig. 2A]
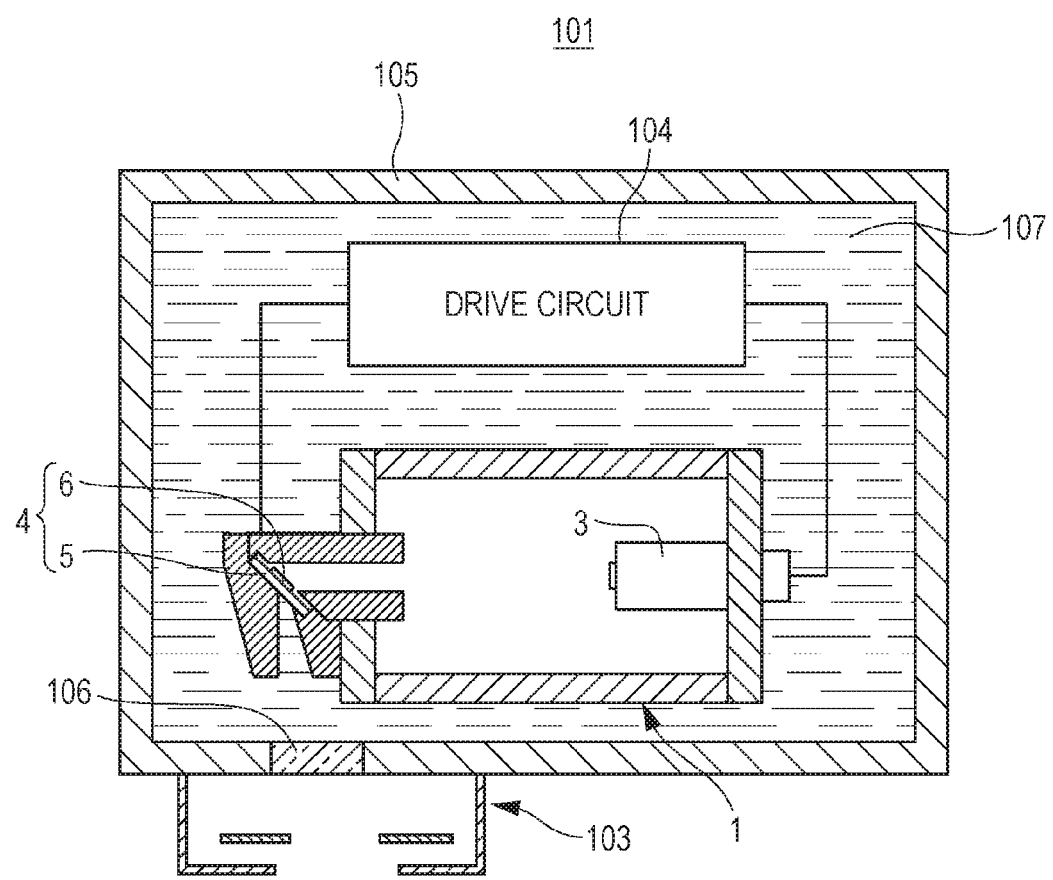

[Fig. 2B]
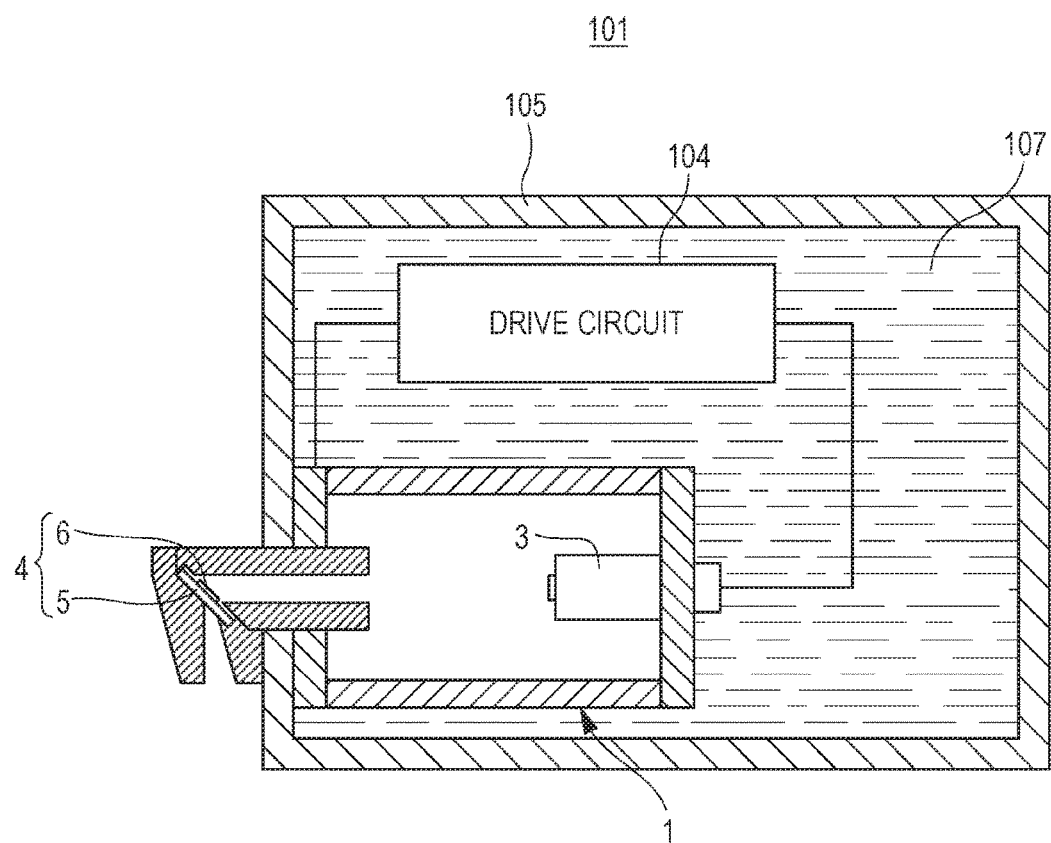

[Fig. 2C]
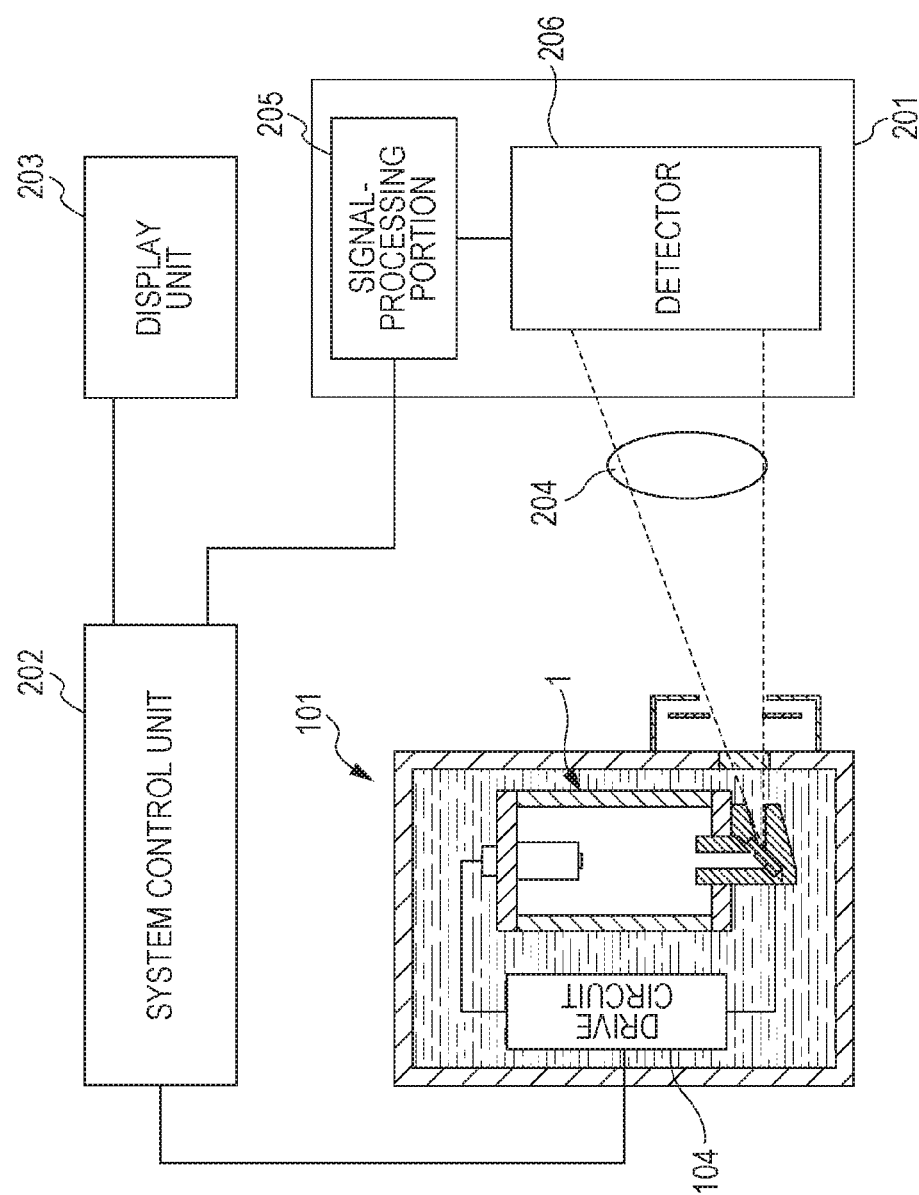

[Fig. 3A]
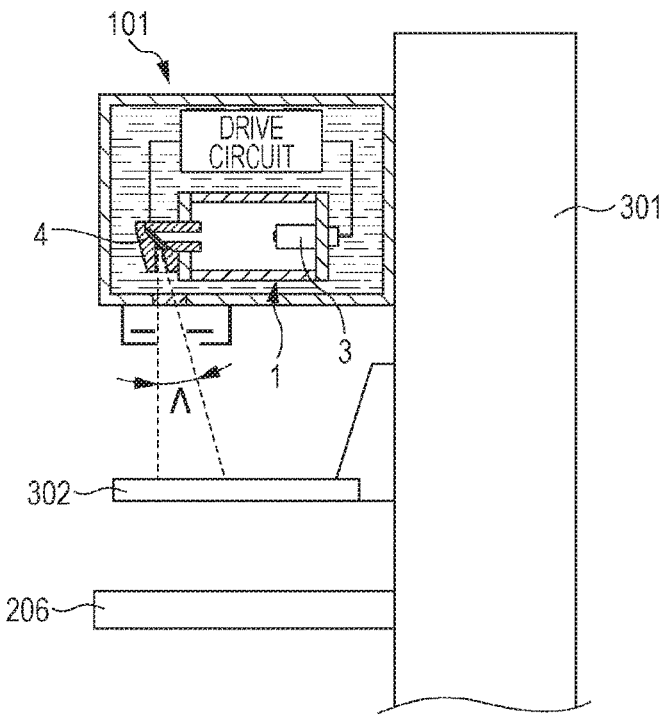
[Fig. 3B]
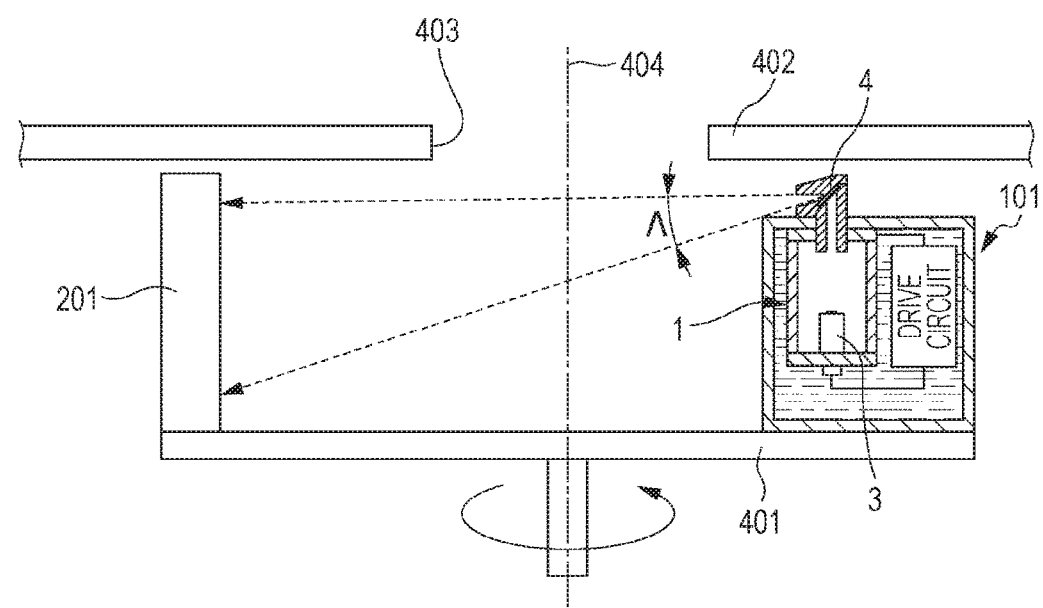

[Fig. 4A]
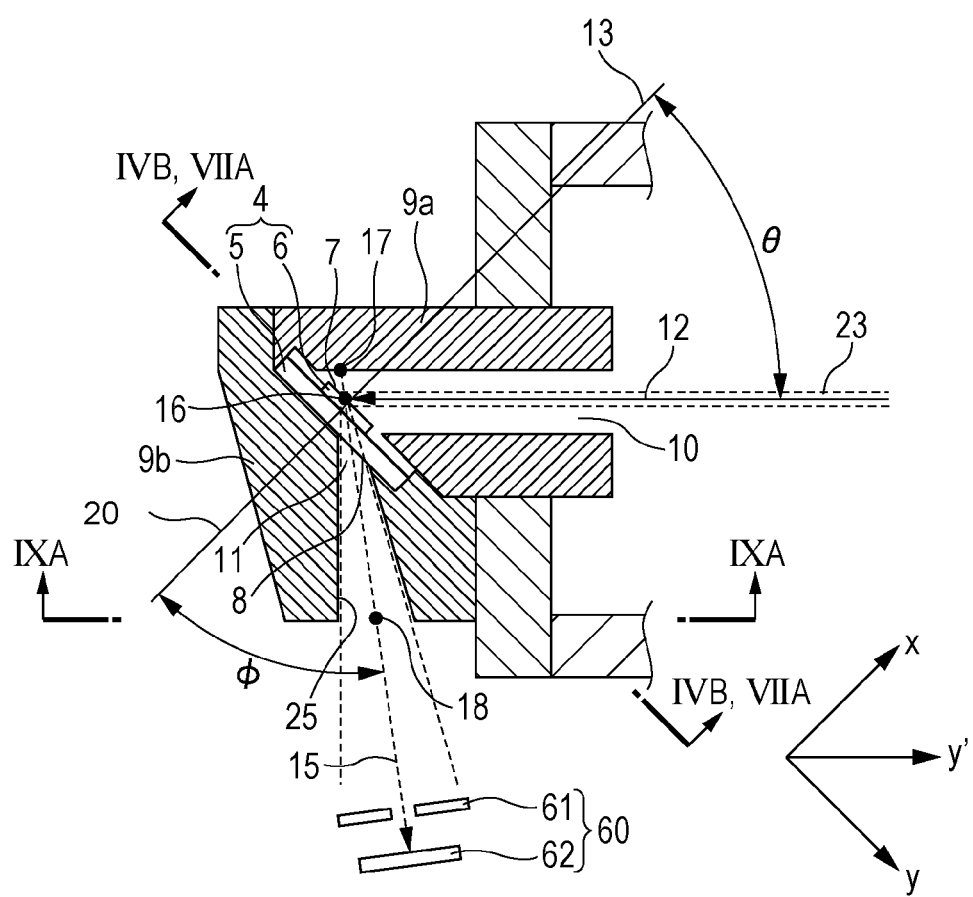

[Fig. 4B]
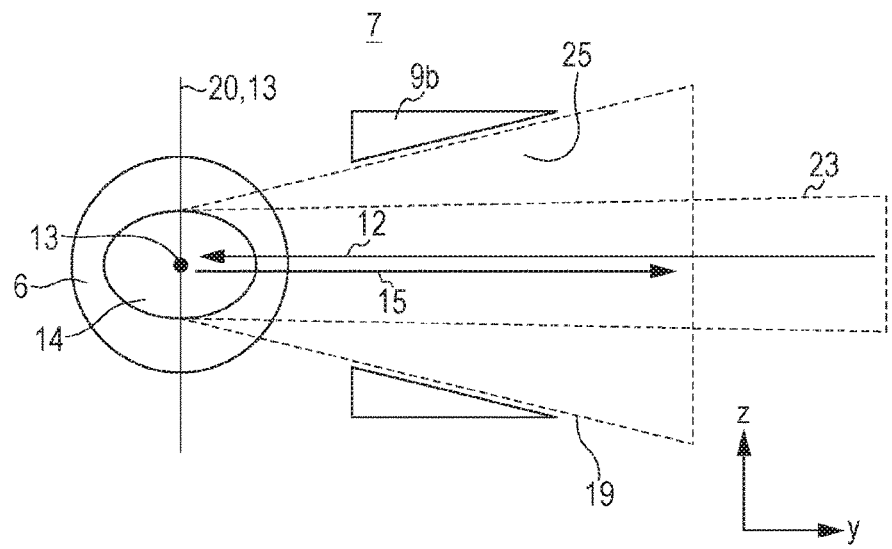
[Fig. 4C]
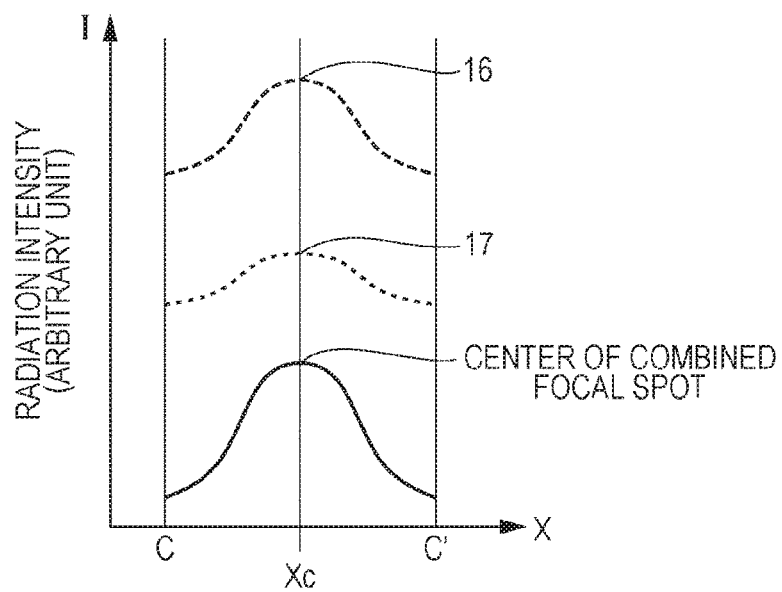

[Fig. 5A]
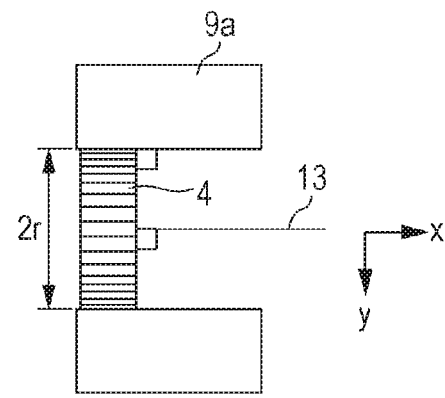
[Fig. 5B]
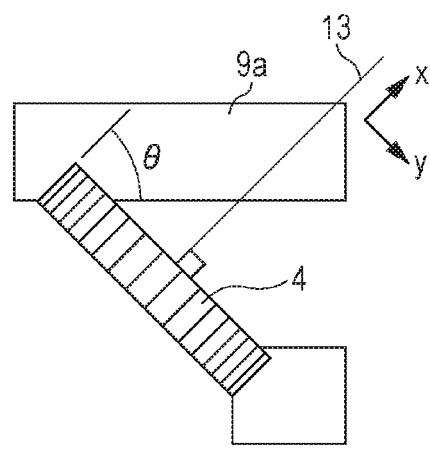
[Fig. 5C]
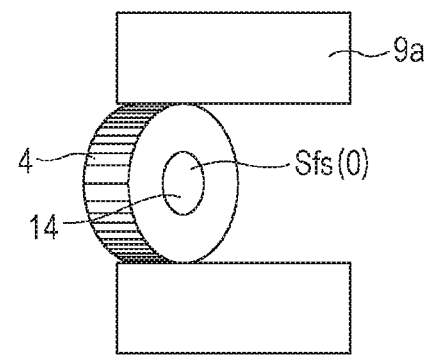

[Fig. 5D]
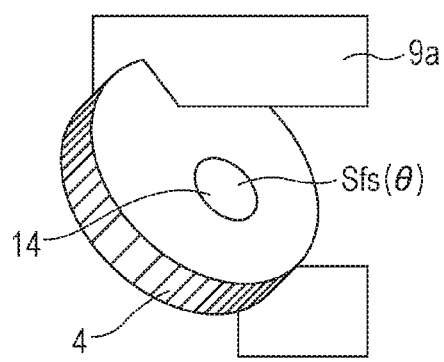
[Fig. 5E]
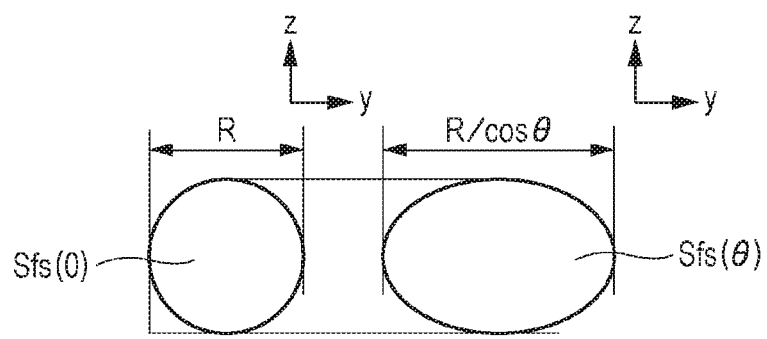
$Sfs(\theta) = Sfs(0)/\cos\theta > Sfs(0)$

[Fig. 6A]
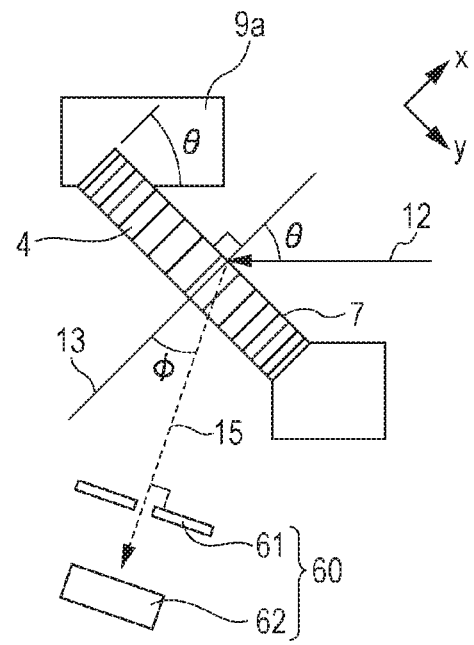
[Fig. 6B]
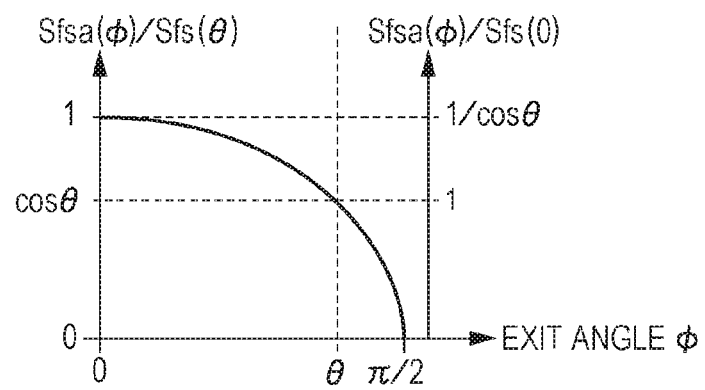

[Fig. 7A]
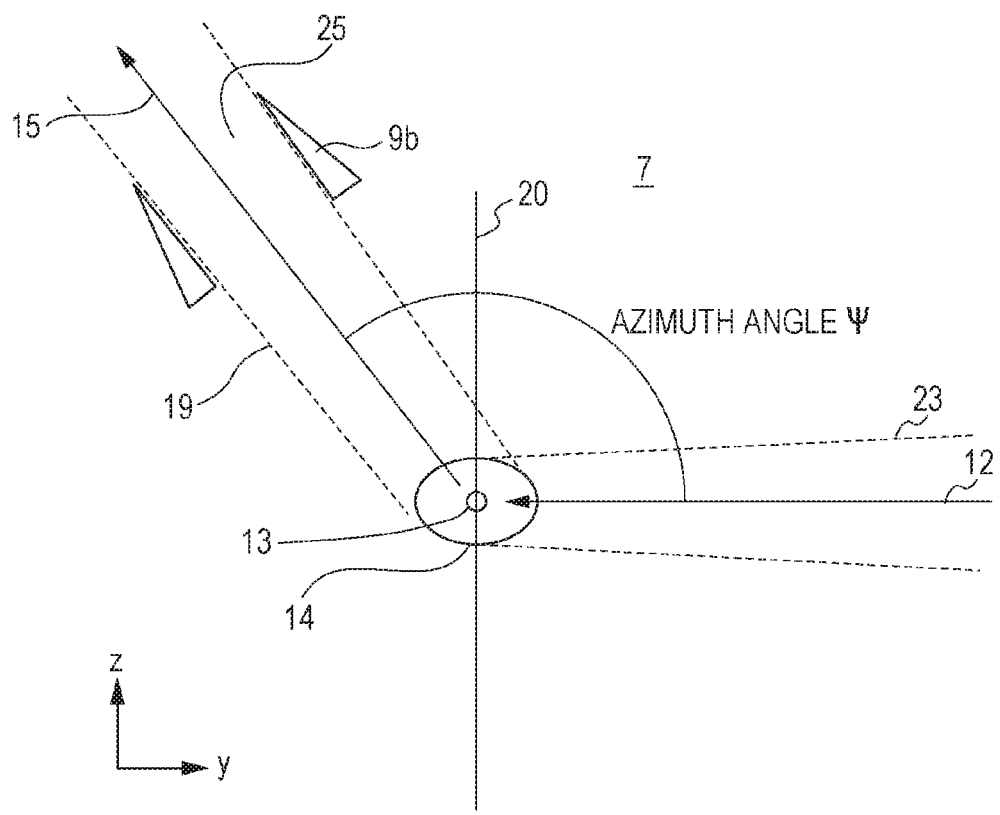

[Fig. 7B]
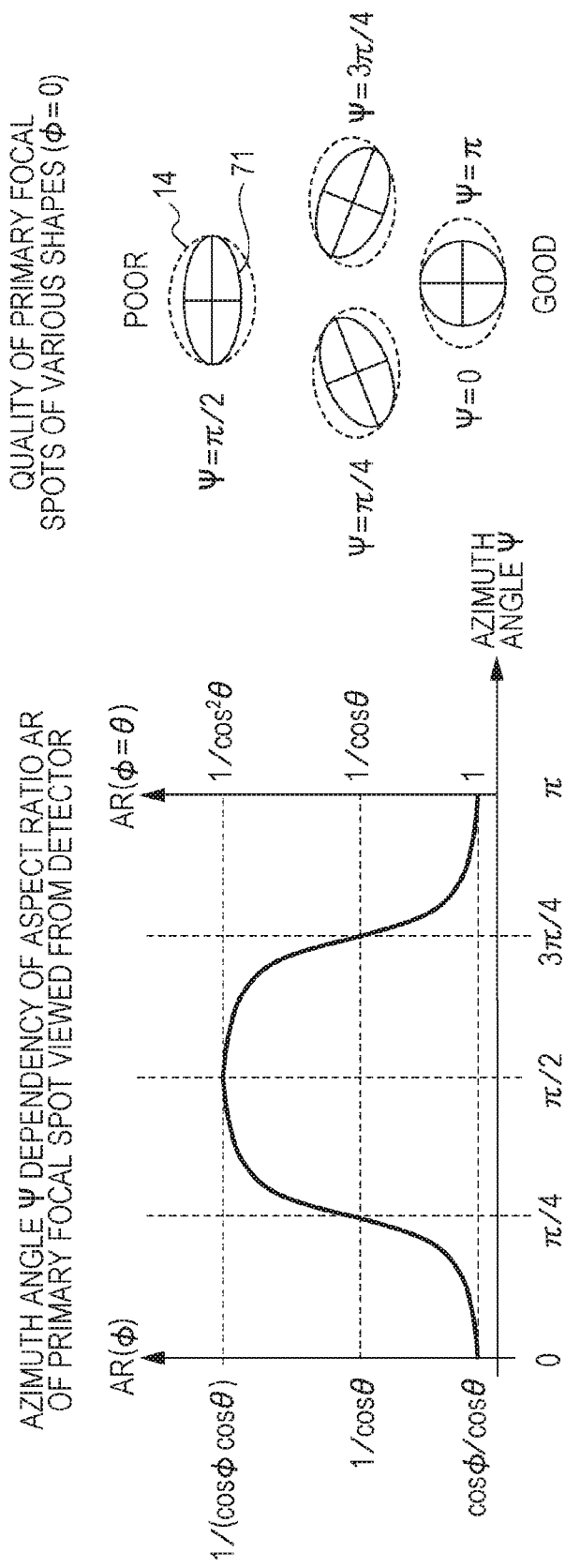

[Fig. 8A]
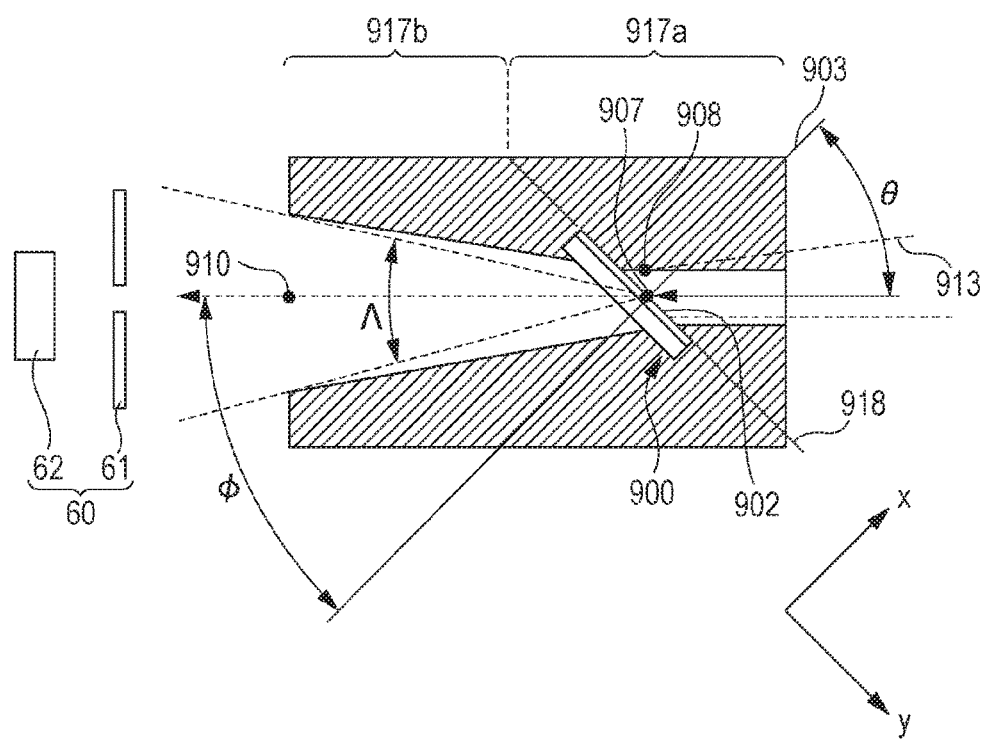

[Fig. 8B]
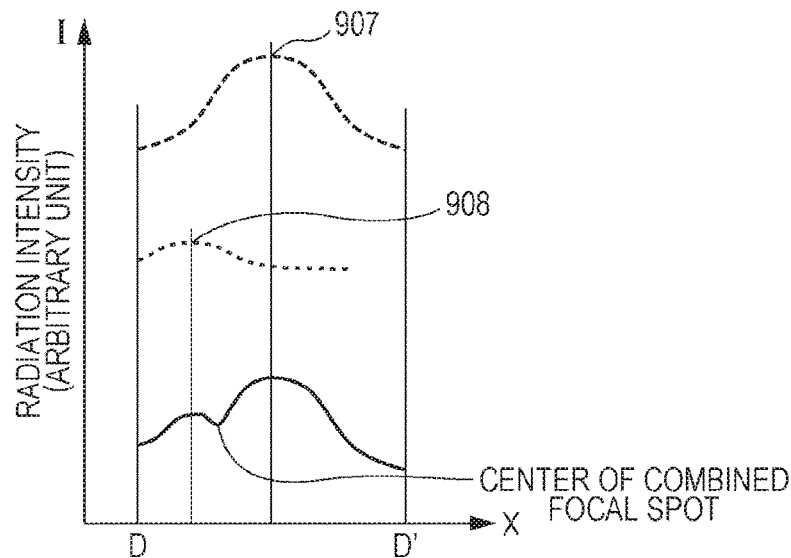
[Fig. 8C]
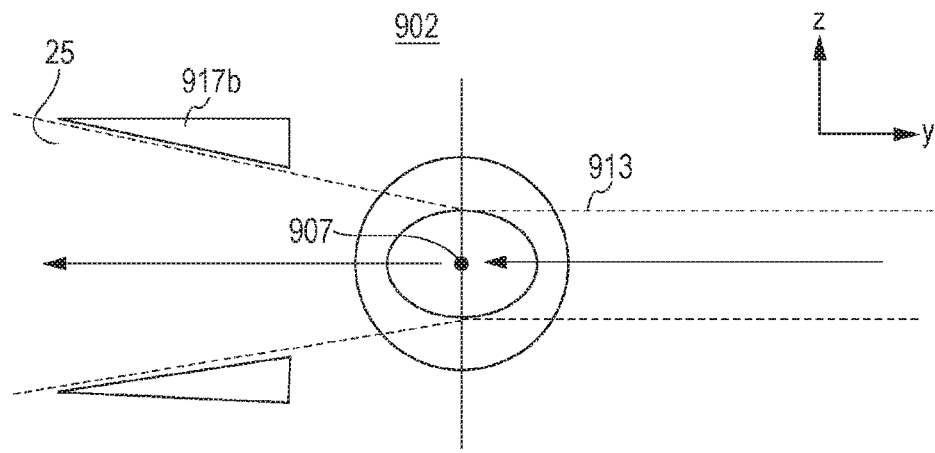

[Fig. 9A]
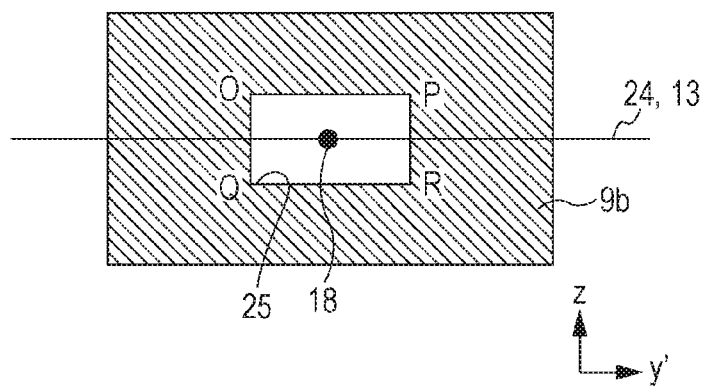
[Fig. 9B]
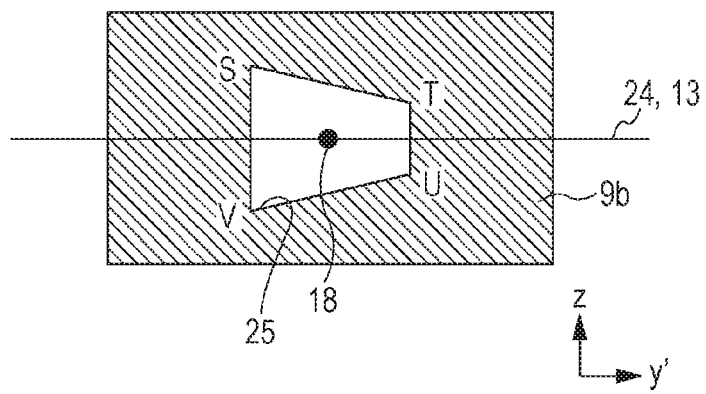

X-RAY GENERATING TUBE, X-RAY GENERATING APPARATUS, AND RADIOGRAPHY SYSTEM

TECHNICAL FIELD

The present invention relates to an X-ray generating tube for use in various imaging operations for, for example, diagnosis in a medical field and nondestructive inspection in an industrial field, as well as an X-ray generating apparatus including the X-ray generating tube and a radiography system including the X-ray generating apparatus.

BACKGROUND ART

Radiography apparatuses equipped with an X-ray generating apparatus are required to detect a minute region in which biological tissue has changed, such as calcified tissue, which is a premonitory symptom of a lesion, by improving imaging resolution to provide high-definition images.

One of the main factors in determining the imaging resolution of X-ray generating apparatuses is the focal spot size of a target serving as an X-ray generation source. In X-ray generating apparatuses that generate X-rays by irradiating a target with an electron beam, the "X-ray generation efficiency" of the target is less than 1%, and most of energy given to the target is converted to heat. Thus, the lower limit of the focal spot diameter of the target actually depends on "anode current density", "heat-resisting performance of the target", "heat-radiating performance of the target", and "X-ray generation efficiency" at the focal point.

A known method for increasing "X-ray generation efficiency" is forming a transmission target with a thin target layer containing heavy metal and a base material that transmits X-rays and supports the target layer. PTL 1 discloses a transmission target of a rotary anode type whose "X-ray generation efficiency" is increased to 1.5 times or more as high as that of a conventional reflection target of a rotary anode type. The X-ray generating tube uses a transmission target that generates X-rays by applying an electron beam to an electron-irradiated surface of the target from an electron emitting source and releases the generated X-rays through an exit surface opposite to the electron-irradiated surface.

A known method for enhancing the "heat-radiating performance" and the "heat-resisting performance" of the transmission target is employing diamond as a base material for supporting a target layer of a transmission target. PTL 2 discloses a method for enhancing the heat-radiating performance by using diamond as abuse material that supports a target layer made of tungsten to form a minute focal spot. Diamond is suitable for the support substrate of the transmission target because of its high heat-resisting performance, high heat-conducting performance, and high X-ray transmitting performance.

Another method for enhancing the "performance" of the transmission target is to hold the target in an anode member so as to reduce the heat resistance of a joint portion between the target and the anode member. PTL 3 discloses an X-ray generating tube including a tubular anode member and a target disposed in an intermediate point of the hole of the tubular anode member obliquely with respect to the longitudinal direction of the hole so as to increase the area of heat transfer, thereby decreasing the heat resistance of the joint portion between the target and the anode member.

CITATION LIST

Patent Literature

PTL 1: PCT Japanese Translation Patent Publication No. 2009-545840

PTL 2: PCT Japanese Translation Patent Publication No. 2003-505845

PTL 3: Japanese Patent Laid-Open No. 2012-124098

SUMMARY OF INVENTION

Technical Problems

The tubular anode member disclosed in PTL 3 serves also as a shield that blocks part of X-rays generated at the target and extracts the X-rays as an X-ray beam having a predetermined radiation angle through one end of the hole. The X-ray generating tube disclosed in PTL 3 further includes a tubular shield that holds the target. The tubular shield includes a backward shield member extending toward the electron emitting source with respect to an electron-irradiated surface of the target, with an electron passage left, and a forward shield member extending toward the electron emitting source, with an X-ray passage left.

However, the X-ray generating tube including the backward shield member and the forward shield member, as disclosed PTL 3, sometimes has the problem of changing in the shape of the focal spot, viewed from an X-ray irradiation area, to increase in the focal spot size as compared with a primary focal spot of an electron beam formed on the electron-irradiated surface.

The present invention provides an X-ray generating tube including a forward shield member and a backward shield member, in which a target is disposed such that its electron-irradiated surface is at an angle with respect to the electron beam axis, and in which deformation of an X-ray intensity distribution and an increase in the focal spot diameter, which hinder size reduction of the focal spot, are reduced. The present invention provides an X-ray generating apparatus and a radiography system in which deformation of an X-ray intensity distribution in an X-ray irradiation area and an increase in a focal spot diameter are reduced.

Solution to Problems

The present invention provides an X-ray generating tube including a transmission target having a first surface and a second surface opposite to the first surface, the first surface being irradiated with an electron beam, and the target generating X-rays from the second surface; an electron emitting source emitting the electron beam in such a manner that the electron beam obliquely enters the first surface; and a tubular forward shield member located at the second surface side of the target to define an extraction angle of an extracted X-ray beam. The forward shield member is disposed such that a central axis of the electron beam and a central axis of the X-ray beam whose extraction angle is defined are located at the same side with respect to a virtual normal plane perpendicular to the first surface and a projection central axis that is a projection of the central axis of the electron beam to the first surface.

The present invention provides an X-ray generating apparatus including the X-ray generating tube according to an embodiment of the present invention; insulating fluid; a container accommodating the X-ray generating tube and the insulating fluid and a drive circuit electrically connected to the X-ray generating tube, the drive circuit applying a voltage signal to the X-ray tube to control generation of X-rays, wherein the insulating fluid is in contact with the X-ray tube and the container.

The present invention provides a radiography system including the X-ray generating apparatus according to an embodiment of the present invention; an X-ray detecting unit configured to detect X-rays radiated from the X-ray generating apparatus and passed through a subject; and a control unit configured to control the X-ray generating apparatus and the X-ray detecting unit cooperatively.

Further features of the present invention will become apparent from the following description of exemplary embodiments with reference to the attached drawings.

Advantageous Effects of Invention

According to an embodiment of the present invention, disposing the central axis of an electron beam incident on a transmission target and the central axis of X-rays to be extracted so as to satisfy specific geometric relationship allows the center of the primary focal spot and the center of the secondary focal spot viewed from an X-ray irradiation area to be aligned. This can reduce an increase in the size of the focal spot due to a secondary focal spot.

BRIEF DESCRIPTION OF DRAWINGS

FIG. 1 is a cross-sectional view of an X-ray tube according to an embodiment of the present invention.

FIG. 2A is a configuration diagram illustrating an X-ray generating apparatus according to an embodiment of the present invention.

FIG. 2B is a configuration diagram illustrating an X-ray generating apparatus according to another embodiment of the present invention.

FIG. 2C is a configuration diagram illustrating a radiography system according to an embodiment of the present invention.

FIG. 3A is a diagram illustrating a mammography system according to an embodiment of the present invention.

FIG. 3B is a diagram illustrating a computed tomographic mammography system according to an embodiment of the present invention.

FIG. 4A is an enlarged cross-sectional view of an anode structure according to an embodiment of the present invention.

FIG. 4B is a projection diagram of an electron-irradiated surface.

FIG. 4C is a graph showing a combined X-ray intensity distribution.

FIG. 5A is a cross-sectional view showing the relation of a connection between a target and a shield relating to a first technical feature of the present invention.

FIG. 5B is a cross-sectional view showing the relation of another connection between the target and the shield relating to the first feature of the present invention.

FIG. 5C is a perspective view of the anode in FIG. 5A.

FIG. 5D is a perspective view of the anode in FIG. 5B.

FIG. 5E is a diagram showing the electron-beam incidence-angle-theta dependency of a primary foal spot area.

FIG. 6A is a cross-sectional view of an anode relating to a second technical feature of the present invention.

FIG. 6B is a graph showing the exit-angle-PHI dependency of an apparent primary focal spot size Sfsa viewed from a detector.

FIG. 7A is a projection diagram of an electron-irradiated surface of an embodiment relating to a third technical feature of the present invention.

FIG. 7B is a graph showing the azimuth-angle-PSI dependency of the aspect ratio of the primary focal spot viewed from a detector.

FIG. 8A is a cross-sectional view of an anode of a reference example having no third technical feature.

FIG. 8B is a graph showing a combined X-ray intensity distribution.

FIG. 8C is a projection diagram of the electron-irradiated surface.

FIG. 9A is a cross-sectional view of a forward shield member according to an embodiment of the present invention.

FIG. 9B is a cross-sectional view of a forward shield member according to another embodiment of the present invention.

DESCRIPTION OF EMBODIMENTS

Referring first to FIG. 1 to FIGS. 3A and 3B, an X-ray generating tube according to an embodiment of the present invention and examples of application of the X-ray generating tube, that is, an X-ray generating apparatus, a radiography apparatus, a mammography system, and a computed tomographic mammography system, will be described.

As shown in FIG. 1, an X-ray generating tube 1 includes an electron emitting source 3 in a vacuum container 2. The electron emitting source 3 generally includes an electron emitting portion 27, a grid electrode, and a lens electrode. The X-ray generating tube 1 further includes a target 4 at a position facing the electron emitting portion 27. The target 4 is a transmission target having the function of generating X-rays and an X-ray transmission property for extracting the generated X-rays in a direction opposite to the electron emitting source 3. The vacuum container 2 may have an extraction window through which the X-rays exit outside the vacuum container 2.

The vacuum container 2 is an air-tight container including an insulating tube, an anode 32, and a cathode 33, described later, whose internal space is decompressed into a vacuum. At least one of the anode 32 and the cathode 33 and the insulating tube are airtightly joined together with a ring-shaped joint. The insulating tube and the anode 32 or the cathode 32 are joined by brazing. The insulating tube may be formed with a ceramic material, such as alumina or zirconia, or a glass material, such as high-strain-point glass.

The electron emitting source 3 and a cathode member 22 made of heat-resisting metal, such as KOVAR (a registered trademark) (an alloy of iron, nickel, and cobalt) or Monel (a registered trademark) (an alloy of nickel and copper), constitute the cathode 33. The cathode 33 is a potential determinant for the X-ray tube 1 opposed to the anode 32 described later and determines the space charge in the vacuum container 2. The electron emitting source 3 and the cathode member 22 are electrically and airtightly joined by brazing or welding. The cathode 33 may also serve as an electrode terminal that establishes electrical connection with a cathode-potential determining node provided outside the X-ray tube 1.

The transmission target 4 is a layered product formed of a target layer 6 made of a target material that generates X-rays by application of electrons and a support substrate 5 that supports the target layer 6 and transmits the X-rays generated from the target layer 6. The transmission target 4 is opposed to the electron emitting source 3 including the electron emitting portion 27 and has the target layer 6 at the side facing the electron emitting source 3. In this description a surface of the transmission target 4 facing the electron emitting source 3 is referred to as an electron-irradiated surface 7, and a surface opposed thereto is referred to as a radiation surface 8.

The support substrate 5 is made of a material having high X-ray transmittance and thermal conductivity. Examples of the support substrate 5 include beryllium, diamond, and silicon carbide.

The target layer 6 is made of a material that generates X-rays by application of electrons. The target layer 6 contains target metal with an atomic number of 42 or greater so as to efficiently generate X-rays. Examples of a metal-containing material for the target layer 6 include pure metal, alloys, solid solutions, metal oxide, metal nitride, and metal carbide. Examples of the target metal include tungsten, tantalum, and molybdenum.

The transmission target 4 constitutes the anode 32 together with an anode member 21 and a shield 9. The anode 32 is a potential determinant for the X-ray tube 1 opposed to the cathode 33, described above, and determines the space charge in the vacuum container 2. The anode 32 of this embodiment also serves as an electrode terminal that establishes electrical connection with an anode-potential determining node provided outside the X-ray tube 1.

The anode member 21 serves both as an electrode and a structural material for the vacuum container 2. The anode member 21 is made of metal, such as KOVAR, Monel, or stainless steel, in consideration of heat resistance in the process of manufacture and in the operation of the X-ray generating tube 1, coefficient-of-linear-expansion matching with an insulating tube, and so on.

The shield 9 is a member disposed close to the target 4 to block a part of unnecessary X-rays generated in the target 4. The shield 9 is made of a heavy metal element, such as tungsten, tantalum, molybdenum, gold, copper, or silver.

The shield 9 is composed of a backward shield member 9a and a forward shield member 9b with respect to the electron-irradiated surface 7 of the target 4.

The backward shield member 9a is a portion of the shield 9 extending from a position intersecting the electron-irradiated surface 7 toward the electron emitting source 3 (hereinafter referred to as "the back of the target" in this description) in such a manner as to enclose the electron-irradiated surface 7 except an electron beam passage 10 that allows an electron beam to pass through.

The forward shield member 9b is a portion of the shield 9 extending from a position intersecting the electron-irradiated surface 7 in a direction away from the electron emitting source 3 (hereinafter referred to as "in front of the target" in this description) in such a manner as to enclose the radiation surface 8 except an x-ray passage 11 that allows X-rays to pass through.

In this embodiment, the backward shield member 9a is connected to an opening in the anode member 21, with its outer periphery enclosed by the anode member 21, to constitute part of the anode 32. For connection between the backward shield member 9a and the anode member 21, airtight and electrical connection is established by brazing, welding, or the like.

The backward shield member 9a has the function of blocking part of X-rays released to the back of the target 4, of X-rays radiated by application of an electron beam 23 to the electron-irradiated surface 7. The backward shield member 9a also has the function of limiting the range of scattering of backward scattered electrons generated at the electron-irradiated surface 7 because of its position close to the target 4.

The forward shield member 9b has an opening 25 that defines the direction and area of radiation of X-rays generated at the target 4. This configuration allows the X-rays that have passed through the forward shield member 9b are extracted forward of the target 4 as an X-ray beam 19 whose extraction angle LAMBDA is defined.

In the embodiment shown in FIG. 1, the backward shield member 9a and the forward shield member 9b are joined together as separate objects. Alternatively, they may be a single object, or at least one of them may be a combined material composed of a plurality of members.

As shown in FIG. 1, the configuration in which the backward shield member 9a and the forward shield member 9b are formed into a single unit such that the electron beam passage 10 and the x-ray passage 11 are located with the transmission target 4 therebetween allows radiation of X-rays generated at the target 4 in unnecessary directions to be effectively blocked. Thus, this embodiment can provide an X-ray tube in which undesired leakage of X-rays is reduced and a compact lightweight X-ray generating apparatus.

Referring next to FIG. 2A, an X-ray generating apparatus 101 according to an embodiment of the present invention will be described.

The X-ray generating apparatus 101 according to the embodiment of the present invention includes the X-ray generating tube 1, insulating fluid 107 in contact with the X-ray generating tube 1, and a container 105 that accommodates them. The X-ray generating apparatus 101 may have a movable x-ray limiting unit 103 as necessary.

First, the X-ray generating apparatus 101 will be described. The X-ray generating apparatus 101 shown in FIG. 2A further includes a drive circuit 104 that drives the X-ray generating tube 1 by applying a voltage signal. The container 105 is a container made of a metal material, such as brass or stainless steel, and has a heat-releasing structure for releasing heat generated in the X-ray tube 1 to the outside of the container 105 through the insulating fluid 107, described later. The container 105 may have the function of reducing discharge between it and various components disposed therearound by connecting with a predetermined potential determining node.

The container 105 may have an extraction window 106 for extracting X-rays emitted from the X-ray tube 1 to the outside, as shown in FIG. 2A. A space in the container 105 is filled with the insulating fluid 107 serving as a cooling medium for the X-ray tube 1. The insulating fluid 107 is in contact with both the X-ray tube 1 and the inner surface of the container 105.

Examples of the insulating fluid 107 include gas and liquid having an electrically insulating property irrespective of its thermodynamic phase. The insulating property of the insulating fluid 107 offers the action of electrical insulation among the container 105, the drive circuit 104, and wires (not shown). Examples of insulating gas include air, nitride, and sulfur hexafluoride ($SF_6$). An example of insulating liquid is electrical insulating oil; specifically, mineral oil, silicon oil, and perfluoropolymer oil.

The drive circuit 104 is electrically connected to the electron emitting source 3 of the X-ray generating tube 1 and the target layer 6 of the target 4 and applies voltage thereto to control generation of X-rays. X-rays generated when an electron beam is emitted from the electron emitting source 3 to the target 4 with the drive circuit 104 pass through the support substrate 5 of the target 4 and are radiated from the X-ray generating tube 1. Although the drive circuit 104 of this embodiment is accommodated in the container 105, the drive circuit 104 may be disposed outside the container 105 by providing the container 105 with an opening through which a driving wire is passed or a connection terminal connected to the driving wire.

FIG. 2B shows a modification of the X-ray generating apparatus 101 shown in FIG. 2A. In this modification, the anode member 3:2 is configured such that part of the backward shield member 9a, except the target 4 and the forward shield member 9b, is accommodated in the container 105. In this modification, the metal member constituting the wall of the container 105 and the outer periphery of the backward shield member 9a are connected so as to transfer heat. This allows heat generated from the target 4 to he efficiently transferred to the container 105 and to be released outside the X-ray generating apparatus 101. The heat-transferring connection is achieved by a joint method that does not significantly hinder heat transfer between the metal components, such as brazing, welding, or thermal fusion.

The X-ray beam 19 radiated from the X-ray generating tube 1 through the opening 25 of the forward shield member 9b irradiates a predetermined X-ray irradiation area.

The X-ray generating apparatus 101 having the X-ray generating tube 1 according to an embodiment of the present invention provides an X-ray beam with a minute focal spot.

Referring next to FIG. 2C, a radiography system according to an embodiment of the present invention will be described. The radiography system according to the embodiment of the present invention includes the X-ray generating apparatus 101, described above, an X-ray detecting unit 201 that detects X-rays that have passed through a subject 204, a system control unit 202, and a display unit 203.

The system control unit 202 controls the X-ray generating apparatus 101 and the X-ray detecting unit 201 cooperatively. The drive circuit 104 outputs various control signal to the X-ray generating tube 1 under the control of the system control unit 202. With these control signals, the radiation state of X-rays to be radiated from the X-ray generating apparatus 101 is controlled. The X-rays radiated from the X-ray generating; apparatus 101 pass through the subject 204 and are detected by a detector 206. The detector 206 converts the detected X-rays to an image signal and outputs the image signal to a signal processing portion 205. The signal processing portion 205 processes the image signal under the control of the system control unit 202 and outputs the processed image signal to the system control unit 202. The system control unit 202 outputs a display signal for displaying an image to the display unit 203 on the bases of the processed image signal. The display unit 203 displays the image based on the display signal on a screen as an image of the subject 204. The X-ray imaging system of an embodiment of the present invention can be used as a radiography system. The radiography system can be used for nondestructive inspection of industrial products and pathological diagnosis of human and animal bodies.

A specific example of the radiography system according to the embodiment of the present invention is a mammography system shown in FIG. 3A. In FIG. 3A, the X-ray generating apparatus 101 according an embodiment of the present invention is mounted to an upper part of a support stand 301, with X-ray radiation directed downward. The X-ray generating apparatus 101 is disposed such that the target 4 is closer to the subject, and the electron emitting source 3 is opposite thereto in the X-ray generating tube 1.

A pressure plate 302 is mounted below the X-ray generating apparatus 101 in such a manner as to be vertically movable along the support stand 301, and the detector 206 is disposed below the pressure plate 302. The detector 206 may be a flat panel detector (FPD). Irradiating the subject or a breast sandwiched between the detector 206 and the pressure plate 302 with X-rays radiated from the X-ray generating apparatus 101 allows a two-dimensional image of the subject to be acquired.

The use of the X-ray mammography system equipped with the X-ray tube 1 of an embodiment of the present invention, as in this embodiment, can increase the accuracy of detection of minute calcification of early-stage breast cancer.

FIG. 3B illustrates an embodiment in which the X-ray generating apparatus 101 shown in FIG. 2B is applied to a cone beam computed tomography scanner (hereinafter referred to as a CBCT scanner) capable of acquiring a three-dimensional image.

This embodiment is a computed tomographic mammography system that acquires a tomographic image of a breast, as shown in FIG. 3B. The computed tomographic mammography system of this embodiment is disposed on a rotating table 401 rotatable about a rotation axis 404 such that the X-ray generating apparatus 101 and the X-ray detecting unit 201 are opposed, with the rotation axis 404 therebetween. The X-ray generating apparatus 101 is disposed, with X-ray radiation directed to the X-ray detecting unit 201. An examination table 402 on which a subject can lie face-down is provided above the X-ray generating apparatus 101 and the X-ray detecting unit 201. The X-ray generating apparatus 101 is disposed such that the target 4 is closer to the examination table 402 (on the subject side) and the electron emitting source 3 is opposite thereto in the X-ray generating tube 1. The examination table 402 has an examination hole 403, through which an image of the breast of the subject placed therein can be acquired, with the subject lying thereon. The examination hole 403 is located between the X-ray generating apparatus 101 and the X-ray detecting unit 201. A three-dimensional image of the subject can be acquired with the CBCT scanner by capturing images from 360-degree directions while rotating the rotating table 401 and processing the image information with a computer.

The embodiment shown in FIG. 3B includes the X-ray generating apparatus 101 shown in FIG. 2B, in which the target 4 and the shield 9 are located outside the vacuum container 2 that constitutes the X-ray tube and outside the container 105 constituting the X-ray generating apparatus. This allows the embodiment to have the heat radiating action of the target 4 through the heat transferring connection with the above-described container 105, described above, and the action of heat exchange with the atmosphere through the shield 9 with the rotation of the X-ray generating apparatus 101. This reduces a thermal load on the target 4, allowing the beam diameter of the primary focal spot formed on the electron-irradiated surface to be decreased more. Thus, the computed tomographic mammography system of this embodiment has an advantage in that the three-dimensional position of an early-stage calcified region of breast cancer can easily be identified.

In this embodiment, the target 4 and the shield 9 are located between the container 105 and the examination table 402. This allows the tomographic mammography system to decrease in a blind area in the vicinity of the base of the breast of the subject, thereby preventing the breastbone from being exposed to the X-ray beam 19 radiated from the focal point of the target 4.

Referring next to FIG. 4A to FIG. 7B, an anode structure including the transmission target, which is a feature of the X-ray generating tube of an embodiment of the present invention, will be described. The anode structure of the X-ray generating tube of the embodiment of the present invention is characterized in the geometrical relationship between the electron beam axis, which is the central axis of an incident electron beam and the axis of an X-ray beam radiated from the target.

FIG. 4A is an enlarged cross-sectional view of the anode structure of the X-ray generating tube 1 shown in FIG. 1A. Line IVB-IVB in FIG. 4A is located in the electron-irradiated surface 7. FIG. 4B is a virtual cross-sectional view of the target 4 taken along line IVB-IVB 4A, viewed from the back of the target 4. In FIG. 4B, an electron beam axis 12, which is the central axis of the electron beam 23, and an X-ray axis 15, which is the central axis of the X-ray beam 19, are orthographically projected in the virtual cross sectional view IVB-IVB. The virtual cross-sectional view IVB-IVB also shows a primary local spot 14, a normal 13 to the primary focal spot 14 starting from the center of the primary focal spot 14, and a virtual normal plane 20 in which a projection axis to which the electron hewn axis 12 is orthographically projected to a virtual plane including the normal 13 is aligned with the normal 13. In other words, as shown in FIG. 4B, the virtual normal plane 20 is a virtual plane that is perpendicular to a projection central axis in which the central axis 12 of the electron beam 23 is projected to the electron-irradiated surface 7 of the target 4 and that is perpendicular to the electron-irradiated surface 7. FIGS. 4A and 4B show the geometrical relationship between the electron beam axis 12 and the X-ray axis 15. FIG. 4B is a diagram explaining the advantages of the present invention, which is given by a third technical feature, described later. The advantages of the third technical feature will be described later.

The center of the primary focal spot 14 is determined so as to coincide with the center of gravity of the area integral of the primary focal spot 14 and is connected to the electron beam axis 12 and the X-ray axis 15. The X-ray beam 19 is regards as having a conical shape having a portion inscribed in a virtual cone defined by the primary focal spot 14 and the opening 25.

The anode structure of this embodiment has first to third technical features.

The first feature is that the X-ray generating tube 1 includes "an electron emitting source emitting the electron beam in such a manner that the electron beam obliquely enters the first surface". The first technical feature corresponds to that the electron beam 23 is incident on the target 4 in such a manner that the electron beam axis 12 forms an incidence angle theta with the normal 13 (virtual normal plane 20) in FIG. 4A. Since FIG. 4A shows the anode structure in a partial enlarged view, the electron emitting source 3 shown in FIG. 1 is omitted.

The second technical feature is that "the X-ray beam is extracted obliquely with respect to the second surface". The second technical feature corresponds to that the forward shield member 9b having the opening 25 at a position where the X-ray beam 19 is to be extracted in such a manner that the X-ray beam 19 forms an exit angle PHI with the normal 13 in FIG. 4A.

The third technical feature is that "the forward shield member is disposed such that a central axis of the electron beam and a central axis of the X-ray beam whose extraction angle is defined are located at the same side with respect to a virtual normal plane perpendicular to the first surface and a projection central axis that is a projection of the central axis of the electron beam to the first surface". The third technical feature corresponds to that the central axis 12 of the electron beam 23 and the central axis 15 of the X-ray beam 19 have a turned-back relationship with respect to the electron-irradiated surface 7 (first surface) of the target 4 in FIGS. 4A and 4B.

Next, the first technical feature will be described with reference to FIGS. 5A to 5E.

FIGS. 5A and 5B are cross-sectional views of embodiments in which the transmission target 4 is connected to the backward shield member 9a so that the electron beam axis 12 are perpendicular and oblique to the electron-irradiated surface 7 of the target 4, respectively. Specifically, the incidence angles of the electron beam axis 12 shown in FIGS. 5A and 5B are 0 degree and theta degrees, respectively. In FIGS. 5A and 5B, the x-axis is parallel to the normal 13 to the electron-irradiated surface 7, and the y-axis is parallel to the electron-irradiated surface 7. FIGS. 5C and 5D show the embodiments in FIGS. 5A and 5B in perspective view, in which the primary focal spots 14 formed by incidence of an electron beam (not shown) and the areas Sfs of the primary focal spots 14 are shown. FIG. 5E is an explanatory diagram illustrating the relationship among the areas Sfs of the primary focal spots 14, shown in FIGS. 5C and 5D, the diameter R of the electron beam, and the incidence angle theta.

FIG. 5E shows that the focal spot 14 expands in size to 1/cos theta times along y-axis, and the area of the focal spot 14 increases to 1/cos theta based on an incidence angle theta of the electron beam axis 12. Thus, the first technical feature of the present invention allows the density of current at the primary focal spot 14 to be reduced without decreasing the density of current generated from the electron emitting source 3, thus allowing a thermal load on the target 4 to be reduced.

Although the shape of the electron beam 23 and the shape of the primary focal spot 14 having an incidence angle theta of 0 in FIGS. 5C to 5E are circular, the effect of decreasing the current density due to the oblique incidence of the electron beam 23 can be provided in any beam/focal spot shape.

Thus, the first technical feature of the present invention offers the technical meaning of reducing the diameter R of the electron beam 23.

Next, the second technical feature will be described with reference to FIGS. 6A and 6B.

FIG. 6A is a schematic configuration diagram in which a beam-profile measuring device 60 for observing the shape of the primary focal spot 14 is provided at a position of an exit angle PHI of the transmission target 4 with respect to the normal 13. FIG. 6B is a graph showing the exit angle PHI dependency of an apparent primary focal spot size Sfsa viewed from a detector.

The beam-profile measuring device 60 shown in FIG. 6A includes a pinhole member having a pinhole with a diameter sufficiently smaller than the focal spot diameter and an X-ray detector 62 having an array of a plurality of X-ray detecting elements. The use of the beam-profile measuring device 60 allows the shape of the X-ray beam 23, that is, the beam diameter and the X-ray intensity distribution of the X-ray beam 23 to be determined, thus providing an apparent focal spot size Sfsa viewed from the X-ray detector 62. Changing the exit angle PHI between the pinhole of the beam-profile measuring device 60 and the center of the primary focal spot 14 gives the exit-angle-phi dependency of the apparent focal spot size Sfsa(phi) viewed from the X-ray detector 62, as shown in FIG. 6B.

In FIG. 6B, the horizontal axis represents the exit angle PHI, and of the two vertical axes, the left vertical axis represents an apparent focal spot size Sfsa(phi) viewed from the X-ray detector 62, normalized with the area Sfs(theta) of a primary focal spot formed on the electron-irradiated surface 7 with an electron beam 23 having an incidence angle theta. The right vertical axis represents an apparent focal spot size Sfsa(phi) viewed from the X-ray detector 62, normalized with the area Sfs(0) of a primary focal spot formed on the electron-irradiated surface 7 with an electron beam 23 having an incidence angle theta of 0.

As shown in FIG. 4A, a geometrical relationship which the exit angle PHI is larger than the incidence angle theta can make the apparent focal spot size Sfsa(PHI) smaller than primary focal spot size an incidence angle theta of 0 Sfs(0). In other words, the size Sfsa(PHI) of the apparent primary focal spot 14 viewed from the X-ray detector 62 can be made smaller than the size Sfs (0) of the primary focal spot 14 formed with the electron beam 23 having an incidence angle theta of 0 depending on the disposition of the opening 25, the target 4, and the electron emitting source 3. This allows the diameter of a focal spot obtained by designing an electronic lens to be reduced in size.

As shown in FIG. 6B, the apparent focal spot size Sfsa(phi) viewed from the X-ray detector 62 decreases monotonically as the exit angle PHI increases and reaches 0 at an exit angle phi of pi/2. On the condition that the exit angle PHI and the incidence angle theta are equal, the normalized Sfsa(phi)/Sfs(0) is 1, thus allowing the size of the focal spot formed on the electron-irradiated surface 7, increased due to the incidence angle theta, to be recovered to that under the condition that the electron beam 23 is not obliquely incident thereon.

In other words, the first technical feature and the second technical feature allow a thermal load on the target 4 to be reduced without decreasing the current density of the focal spot and without increasing the focal spot size viewed from the X-ray detector 62, thus allowing the electron beam 23 to be decreased in diameter to provide a minute focal spot.

Next, the third technical feature will be described with reference to FIGS. 7A and 7B and FIG. 4B. The third technical feature offers first technical meaning on the quality of the shape of the primary focal spot 14 and second technical meaning on a secondary focal spot generated outside the primary focal spot 14 to the X-ray generating apparatus 1 of the present invention. The secondary focal spot is also referred to as an off-focal spot.

Referring first to FIGS. 7A and 7B, the third technical feature that offers the first technical meaning will be described. FIG. 7A is a virtual cross-sectional view of the electron-irradiated surface 7 taken along line VIIA-VIIA in FIG. 4A, to which the electron beam 23 and the X-ray beam 19 are orthographically projected, FIG. 7B is a graph showing the azimuth-angle-PSI dependency of the aspect ratio AR of the primary focal spot 14 viewed from the X-ray detector 62.

FIG. 7A shows projections of the electron beam axis 12, the X-ray axis 15, the forward shield member 9b, and the opening 25, as well as the primary focal spot 14. FIG. 7A also shows the virtual normal plane 20 in which an orthographical projection of the electron beam axis 12 to a virtual plane including the normal 13 is aligned with the normal 13. For the purpose of understanding, assume that the shape of the electron beam 23 having the electron beam axis 12 shown in FIG. 7A is circular. The target layer 6 formed in a range including the primary focal spot 14 is omitted in FIG. 7A for understanding.

FIG. 7A illustrates the primary focal spot 14 formed on the electron-irradiated surface 7 by incidence of the electron beam 23 at the incidence angle theta. The primary focal spot 14 shown in FIG. 7A has an oval shape extending in the y-axis direction.

Define a difference in angle about the normal 13 between the electron beam axis 12 and the X-ray axis 15 as an azimuth angle PSI. The azimuth angle PSI is defined by the positional relationship among the target 4, the electron emitting source 3, and the opening 25 of the forward shield member 9b. The primary focal spot 14 takes on the shapes shown at the right of FIG. 7B as apparent primary focal spots 71 viewed from the X-ray detector 62 depending on the azimuth angle PSI and the exit angle PHI. FIG. 7B shows that the aspect ratio of the primary focal spot 71 viewed from the X-ray detector 62 changes depending on the azimuth angle PSI.

The aspect ratio of the primary focal spot 71 viewed from the X-ray detector 62 influences on the quality of images taken by the radiography apparatus and is preferably 1. The condition on the azimuth angle PSI for the aspect ratio of 1 of the primary focal spot 71 viewed from the X-ray detector 62 is 0, pi(rad).

Thus, the first technical meaning offered by the third technical feature can be obtained by aligning the electron beam 23 and the X-ray beam 19 while satisfying the relationship of parallel vectors (PSI=pi) or antiparallel vectors (PSI=0). The quality on the shape of the primary focal spot 14 viewed from the X-ray detector 62 can be improved by defining the positional relationship among the target 4, the electron emitting source 3, and the opening 25 of the forward shield member 9b so that the electron beam 23 and the X-ray beam 19 are aligned, with the above relationship satisfied.

Referring next to FIGS. 4A to 4C and FIGS. 8A to 8C, the third technical feature that offers the second technical meaning will be described.

The third technical feature that offers the second technical meaning is that the azimuth angle PSI is set to 0 rad, in other words, the third technical feature that offers the second technical meaning is that the target 4, the electron emitting source 3, and the opening 25 are disposed so that projections of the electron beam 23 and the X-ray beam 19 to the electron-irradiated surface 7 are aligned with each other in an antiparallel vector relationship in FIG. 4B.

In FIG. 4B, the projections of the X-ray beam 19 and the electron beam 23 to the electron-irradiated surface 7 are aligned. In the anode structure of the embodiment shown in FIG. 4A, the opening 25 of the forward shield member 9b is disposed with respect to the target 4 and the electron beam 23 so that the optical geometry shown in FIG. 4B is satisfied.

The X-ray intensity distribution in the vicinity of the center 16 of the primary focal spot 14 of the anode structure of this embodiment that satisfies such optical geometry is shown by the solid line in FIG. 4C. The horizontal axis X in FIG. 4C indicates a direction included in a virtual plane including the normal 13 and the X-ray axis 15 and perpendicular to the X-ray axis 15. Sign Xc on the horizontal axis X corresponds to a position where the X-ray axis 15 and the X-ray detector 62 coincide.

The profile of the solid line (the first line from the bottom) in FIG. 4C can be obtained with the beam-profile measuring device 60 disposed on an extension of the X-ray axis 15. In this specification, a beam profile measured with the beam-profile measuring device 60 disposed on the X-ray axis 15 of the transmission X-ray tube 1 including the backward shield member 9a, the transmission target 9b, and the forward shield member 9b is referred to as "combined X-ray intensity distribution".

The broken-line profile (the first line from the (op) is the beam profile of X-rays radiated through the primary focal spot 14 and is obtained by applying the electron beam 23 to an anode structure (not shown) without the backward shield member 9a. Since the broken-line profile is caused by the electron-irradiated surface 7 and is not influenced by the backward shield member 9a, it is referred to as "X-ray intensity distribution of the electron-irradiated surface".

A close examination of the inventors shows that the "combined X-ray intensity distribution" and the "X-ray intensity distribution of the electron-irradiated surface" do not coincide in beam profile; the former shows higher intensity than the latter. The difference between the "combined X-ray intensity distribution" and the "X-ray intensity distribution of the electron-irradiated surface" is expressed as the doted-line profile (the second line from the top) and has a maximum component at a predetermined X-coordinate. The examination also shows that the X-coordinate indicating the maximum component of the dotted-line profile changes depending on the mutual positional relationship of the backward shield member 9a with the transmission target 4 and the opening 25.

Thus, it has been determined that the dotted-line profile depends on the backward shield member 9a. In this description, the dotted-line profile is referred to as "X-ray intensity distribution of the backward shield member". The average of the "X-ray intensity distribution of the backward shield member" is a few percent or lower of the "X-ray intensity distribution of the electron-irradiated surface". However, it has been determined that the "combined X-ray intensity distribution", viewed from the beam-profile measuring device 60, is deformed with respect to the center 16 of the primary focal spot 14 depending on the position of the backward shield member 9a, as shown by the solid line in FIG. 8B.

A mechanism presumed for the "X-ray intensity distribution of the backward shield member" that causes distortion in the "combined X-ray intensity distribution" as a result of close examination of the inventors will be described with reference to FIGS. 8A to 8C.

Referring to FIG. 8A, part of an electron beam 913 applied to an electron-irradiated surface 902 scatters to the back of a target 900 as backward scattered electrons. The backward scattered electrons scatter with a scattering angle distribution centered on a reflection angle theta' (=theta) that is an angle turned about a normal 903 according to a cosine law, p (theta') proportional to cos (theta'). Since the passage of the electron beam 913 is a field-free area due to the metallic shield, the elastically scattered backward electrons travel without decreasing in speed to collide with the backward scattered electrons.

This causes the "X-ray intensity distribution of the backward shield member" having the maximum at a predetermined detection position and the center 908 of a secondary focal spot to be formed in a backward shield member 917a.

In the embodiment shown in FIG. 8A in which an extension of the center 908 of the secondary focal spot and the center 907 of the primary focal spot passes through an opening of a forward shield member 917b and does not pass through the opening center 910 of the forward shield member 917b, the "combined X-ray intensity distribution", as shown in FIG. 8B, is provided. Each of the forward shield member 917b and the backward shield member 917a is assigned with an imaginary plane 918 including the electron-irradiated surface 7.

In FIG. 8B, the X-coordinate of the center 908 of the secondary focal spot, which is the center of intensity of the "X-ray intensity distribution of the backward shield member" and the X-coordinate of the center 907 of the primary focal spot, which is the center of intensity of the "X-ray intensity distribution of the electron-irradiated surface", do not coincide, thus causing distortion in the "combined X-ray intensity distribution". Thus, to obtain the third technical feature that offers the second technical meaning, the X-ray generating tube 1 may be configured such that the opening 25 is located at the electron emitting source 3 side with respect to the virtual normal plane 20 in which an orthogonal projection of the electron beam 23 to a virtual plane including the normal 13 of the target 4 and the center 16 of the primary focal spot 14 is aligned with the normal 13, as shown in FIGS. 4A and 4B and FIG. 1.

To ensure the third technical feature that offers the second technical meaning, the X-ray generating tube 1 may be configured such that a straight line connecting the center 17 of the secondary focal spot formed oil the backward shield member 9a when backward scattered electrons scattered backwards through the primary focal spot 14 due to application of the electron beam 23 are incident on the backward shield member 9a and the center 16 of the primary focal spot 14 passes through the opening 25, as shown in FIG. 4A.

Referring to FIGS. 9A and 9B, the shape of the opening 25 of the forward shield member 9b in the case where the X-ray generating tube 1 with the anode structure shown in FIG. 4A is applied to the mammography system shown in FIG. 3A and the computed tomographic mammography system shown in FIG. 3B will be described.

In the embodiment shown in FIG. 4A, the x-ray passage 11 gradually increases in diameter toward the distal end, and the inner wall of the opening 25 constituting the x-ray passage 11 is formed of four flat surfaces. FIG. 9A shows a cross-sectional view of the embodiment shown in FIG. 4A taken along line IXA-IXA.

FIG. 9A illustrates the/onward shield member 9b having a rectangular opening 25 having vertices O, P, Q, and R and the normal 13 orthographically projected to the cross section IXA-IXA. In this embodiment, two opposing sides PR and OQ that define the opening 25 are perpendicular to a projection normal 24, thus allowing the detection range of a generally rectangular X-ray detector (not shown) and the irradiation range of the X-ray generating apparatus 101 to be aligned with high accuracy.

FIG. 9B shows a modification of the embodiment shown in FIG. 9A, in which the forward shield member 9b includes a trapezoidal opening 25 having vertices S, T, U, and V. The two sides TU and SV defining the opening 25 are perpendicular to the projection normal 24. In the case where the detection surface of an X-ray detector (not shown) and the central axis 15 of the X-rays are not perpendicular to each other, the radiation range that becomes trapezoidal with an increase in the size of the X-ray beam with increasing distance from the focal spot can be corrected by adjusting the length ratio of the side TU to the side SV.

In the embodiment shown in FIGS. 1 and 4A, the primary focal spot 14 formed on the target layer 6 with the electron beam 23 is away from the backward shield member 9a. In contrast to this embodiment, with the X-ray tube 1 that applies the electron beam 23 to the target layer 6 and the backward shield member 9a at the same time, parameters of the target layer 6 and the backward shield member 9a, such as the densities, constituent elements, compositions, and angles to the electron beam 23, differ. This causes the elementary process of scattering of electrons to differ between the medium of the target layer 6 and the medium of the backward shield member 9a. This causes the quality of radiation on the target layer 6 and the backward shield member 9a to differ, which causes an off-focal spot, thus increasing the focal spot size effectively.

Thus, the X-ray generating tube may be separated from the backward shield member 9a as in the embodiment shown in FIGS. 1 and 4A to make the primary focal spot 14 minute.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-193903, filed Sep. 19, 2013, which is hereby incorporated by reference herein in its entirety.

The invention claimed is:

1. An X-ray generating tube comprising:
   a transmission target having a surface configured to be irradiated with an electron beam and generate X-rays;
   an electron emitting source configured to irradiate the surface with the electron beam and form a primary focal spot;
   a tubular backward shield member having an electron beam passage and located at the surface side of the transmission target; and
   a tubular forward shield member located in opposition to the surface side of the transmission target configured to define an extraction angle of an extracted X-ray beam,
   wherein the tubular backward shield member is connected to the tubular forward shield member,
   wherein the X-ray beam is extracted obliquely with respect to the surface; and
   the tubular forward shield member is disposed such that a central axis of the electron beam and a central axis of the X-ray beam are located at a same side with respect to a virtual normal plane perpendicular to the surface and a projection of the central axis of the electron beam to the surface and intersecting the primary focal spot.

2. The X-ray generating tube according to claim 1, wherein the electron beam travels to the surface on one side of the virtual normal plane and the X-ray beam travels away from the surface on the one side of the virtual normal plane such that both the electron beam and the X-ray beam travel in different directions with respect to the one side of the virtual normal plane.

3. The X-ray generating tube according to claim 2, wherein a projection of the electron beam to the surface is aligned with a projection of the X-ray beam to the surface from an off-focal spot.

4. The X-ray generating tube according to claim 1, wherein the forward shield member has an opening through which part of the X-rays radiated from the target passes, and wherein the opening is located at the electron emitting source side with respect to the virtual normal plane.

5. The X-ray generating tube according to claim 4, wherein the extraction angle of the X-ray beam is defined by the opening.

6. The X-ray generating tube according to claim 4, wherein the X-ray beam has a cone shape having a portion inscribed in a virtual cone defined by the primary focal spot and the opening.

7. The X-ray generating tube according to claim 1, wherein the backward shield member projects from the periphery of the target toward the electron emitting source.

8. The X-ray generating tube according to claim 1, wherein a straight line connecting a center of a secondary focal spot formed on the backward shield member when backward scattered electrons scattered at the primary focal spot enter the backward shield member and a center of the primary focal spot passes through the opening.

9. The X-ray generating tube according to claim 1, wherein an exit angle PHI that the central axis of the X-ray beam forms with the virtual normal plane is larger than an incidence angle theta that the central axis of the electron beam forms with the virtual normal plane.

10. The X-ray generating tube according to claim 1, wherein the backward shield member and the forward shield member are integrated to a single unit.

11. The X-ray generating tube according to claim 1, wherein an opening of the forward shield member is trapezoidal or rectangular.

12. The X-ray generating tube according to claim 11, wherein two opposing sides that defines the opening are perpendicular to a normal to the primary focal spot.

13. The X-ray generating tube according to claim 1, wherein the primary focal spot is spaced apart from the backward shield member.

14. An X-ray generating apparatus comprising:
   the X-ray generating tube according to claim 1;
   insulating fluid;
   a container accommodating the X-ray generating tube and the insulating fluid; and
   a drive circuit electrically connected to the X-ray generating tube, the drive circuit applying a voltage signal to the X-ray tube to control generation of X-rays,
   wherein the insulating fluid is in contact with the X-ray tube and the container.

15. The X-ray generating apparatus according to claim 14, wherein
   the container has an opening; and
   the outer periphery of the backward shield member is connected to the opening of the container so as to transfer heat.

16. The X-ray generating apparatus according to claim 14, wherein the container accommodates the drive circuit.

17. A radiography system comprising:
   the X-ray generating apparatus according to claim 14;
   an X-ray detecting unit configured to detect X-rays radiated from the X-ray generating apparatus and passed through a subject; and
   a control unit configured to control the X-ray generating apparatus and the X-ray detecting unit cooperatively.

18. The radiography system according to claim 17, wherein the subject is a breast.

19. The radiography system according to claim 17, wherein the X-ray generating apparatus is disposed in such a manner so as to be rotatable around a breast to acquire a tomographic image of the breast.

* * * * *